(12) United States Patent
Bier et al.

(10) Patent No.: US 7,402,566 B2
(45) Date of Patent: Jul. 22, 2008

(54) PEPTIDE INHIBITOR OF TGF-β GROWTH FACTORS

(75) Inventors: Ethan Bier, San Diego, CA (US); Kweon Yu, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 625 days.

(21) Appl. No.: 10/944,480

(22) Filed: Sep. 17, 2004

(65) Prior Publication Data

US 2006/0003929 A1 Jan. 5, 2006

Related U.S. Application Data

(62) Division of application No. 09/215,569, filed on Dec. 16, 1998, now Pat. No. 6,806,358.

(60) Provisional application No. 60/069,701, filed on Dec. 16, 1997.

(51) Int. Cl.
C07K 14/475 (2006.01)
A61K 38/18 (2006.01)

(52) U.S. Cl. .................... 514/12; 530/350

(58) Field of Classification Search .................... None
See application file for complete search history.

(56) References Cited

OTHER PUBLICATIONS

Bowie et al. Deciphering the message in protein sequences: tolerance to amino acid substitutions. Science, (Mar. 16, 1990) 247 (4948) 1306-10.*
Ngo et al., in Protein Folding Problem and Tertiary Structure Prediction, Merz and Le Grand (Eds), Aug. 1994, Springer Verlag, pp. 433 and 492-495.*
Biehs, B., et al., "The *Drosophila short gastrulation* gene prevents Dpp from autoactivating and suppressing neurogenesis in the neuroectoderm," *Gene & Development* (1996) 10:2922-2934.
Bier, E., "Anti-Neural-Inibition: A Conserved mechanism for Neural Induction," *Cell* May 30, 1997; 89:681-684.
Cork, MJ, et al., "Genetic control of cytokines. Cytokine gene polymorphisms in alopecia areata," *Dermatol Clin* Oct. 1996;14(4):671-678.
Danilenko DM, et al., "Growth factors and cytokines in hair follicle development and cycling: recent insights from animal models and the potentials for clinical therapy," *Mol Med Today* Nov. 1996;2(11):460-467.
François, V., et al., "Dorsal-ventral patterning of the *Drosophila* embryo depends on a putative growth factor encoded by the *short gastrulation* gene," *Genes & Development* (1994) 8:2602-2616.
François, V., et al., "*Xenopus chordin* and *Drosophila short gastrulation* Genes Encode Homologous Proteins Functioning in Dorsal-Ventral Axis Formation," Letters to the Editor, *Cell* Jan. 13, 1995; 80:19-20.
Genbank Accession No. AA140772, Jan. 25, 1997.
Genbank Accession No. L35764, Dec. 22, 1994.
Hoffmann, R., et al., "Growth factor mRNA levels in alopecia areata before and after treatment with the contact allergen diphenylcyclopropenone," *Acta Derm Venereol* Jan. 1996; 76(1):17-20.
Honda, Y., et al, "Osteogenic protein-I stimulates mRNA levels of BMP-6 and decreases mRNA levels of BMP-2 and -4 in human osteosarcoma cells," *Calcif Tissue Int* Mar. 1997; 60(3):297-301.
Imai, R., et al., "Effects of cytokines, anti-cancer agents and coarcinogen on DNA synthesis in hair bulb cells," *J Dermatol Sci* Apr. 1993;5(2):73-80.
King, LE Jr, et al., "Growth factor receptors and hair loss." *J Invest Dermatol* May 1991;96(5):79S.
Konig, A., et al., "IFN-gamma-induced HLA-DR but not ICAM-1 expression on cultured dermal papilla cells is downregulated by TNF-alpha," *Arch Dermatol Res* Jul. 1997; 289(8): 466-470.
Kweon, Y., et al., "The *Drosophila decapentaplegic* and *short gastrulation* genes function antagonistically during adult wing vein development," *Development* (1996) 122:4033-4044.
Murillas, R., et al., "Expression of a dominant negative mutant of epidermal growth factor receptor in the epidermis of transgenic mice elicits striking alterations in hair follicle development and skin structure." *EMBO J* Nov. 1, 1995;14(21):5216-5223.
Nishitoh H., et al., "Identification of type I and type II serine/threonine kinase receptors for growth/differentiation factor-5," *J Biol Chem* Aug. 30, 1996; 271(35):21345-21352.
Philpott, MP, et al., "Cultured human hair follicles and growth factors," *J Invest Dermatol* May 1995;104(5 Suppl)44S-45S.
Phippard, DJ, et al., "Regulation of Msx-1, Msx-2, Bmp-2 and Bmp-4 during foetal and postnatal mammary gland development," *Development* Sep. 1996; 122(9):2729-2737.
Sanchez-Carpintero, et al., "Role of neuropeptides in dermatology," *Rev Neurol* Sep. 1997;25 Suppl 3:S222-S231.
Schmidt, J., et al., "*Drosophila short gastrulation* induces an ectopic axis in *Xenopus*: evidence for conserved mechanisms of dorsal-ventral patterning," *Development* (1995) 121:4319-4328.
Sturtevant, Mark A., et al., "The *spalt* gene links the A/P compartment boundary to a linear adult structure in the *Drosophila* wing," *Development* 124, 21-32 (1997).
Wu, X., et al., "Analysis of the native murine bone morphogenetic protein serine threonine kinase type I receptor (ALK-3)" *J. Cell Physiol* Aug. 1996; 168(2):453-461.
Xu, RH, et al., "Differential regulation of neurogenesis by the two Xenopus GATA-1 genes," *Mol Cell Biol* Jan. 1997; 17(1):436-443.
Zavadil, J., et al., "Smad5, a tumor suppressor candidate at 5q31.1, is hemizygously lost and not mutated in the retained allele in human leukemia cell line HL60," *Leukemia* Aug. 1997;11(8):1187-1192.
Marques et al., Production of a DPP activity gradient in the early Drosophila embryo through the opposing actions of the SOG and LTD proteins. Cell. 91(3): 417-426, 1997.
Sambrook et al. Molecular Cloning: A Laboratory Manual. Second edition. vols. 1, 2 and 3. Cold Spring Harbor Laboratory Press: Cold Spring Harbor, New York, U.S.A. Nov. 1989. p. 11.20.

* cited by examiner

*Primary Examiner*—David S Romeo
(74) *Attorney, Agent, or Firm*—DLA Piper US LLP

(57) ABSTRACT

A potent peptide inhibitor (SuperSog) of TGF-β family growth factor signaling, peptide variants thereof and nucleotide coding sequences therefore are provided by the invention. The Super-Sog peptide comprises a fragment of the *Drosophilia* short gastrulation (Sog) gene which includes the CR-1 cysteine-rich repeat of Sog. Methods and compositions for use of Super-Sog in therapeutic and diagnostic applications are also provided.

2 Claims, No Drawings

SEQUENCE LISTING

<160> NUMBER OF SEQ ID NOS: 12

<210> SEQ ID NO 1
<211> LENGTH: 879
<212> TYPE: DNA
<213> ORGANISM: Drosophila Short Gastrulation Gene (SOG)

<400> SEQUENCE: 1

```
atggccaaca agctgaggaa atcgaacgcc atcgaatggg ccagcgccac cggcacagta      60
ccgctcctgg aaaggagctg ctgccacacg gaggacgccg cactggagcc caagcgagc     120
aaaaccagcc atagagaaca agcccccatc ctgcgccacc tgagccaact gagccacctg    180
ctcatcatcg ccccactgct gatcgtctgc ttgcgcccgg tgacggaggg ccgccggcat    240
gcgccgctca tgttcgagga gtccgacacg ggcaggcggt ccaaccgacc agcggtcacc    300
gaatgccagt ttggcaaagt tttgcgcgaa ttggggtcca cctggtatgc ggatttgggt    360
ccacccttcg gagttatgta ctgcatcaag tgtgaatgtg tggcgatacc aagaagcgg     420
cgcatcgttg cacgcgtcca gtgtgcgaat atcaaaaacg agtgcccgcc ggccaaatgc    480
gatgatccca tctcgttgcc cggaaaatgc tgcaagacct gtcccggcga tcgaaacgat    540
acggatgtag ccttggatgt gcccgtgccc aatgaagagg aagagcgcaa catgaaacat    600
tacgctgcgt tgctaacggg ccgcacctcc tatttcctca agggtgagga aatgaagtcc    660
atgtacacca cctacaatcc gcagaatgtg gtggccaccg cccgtttcct gttccacaag    720
aagaatctat actactcctt ctacacctca tcgcgaatcg gtcgtccgcg tgccattcaa    780
ttcgttgatg atgcgggtgt aatcctggag gagcatcaac tggagaccac cttgcgcggc    840
actctcagtg tctatcagaa tgccacgggc aagatctga                           879
```

<210> SEQ ID NO 2
<211> LENGTH: 292
<212> TYPE: PRT
<213> ORGANISM: Drosophila Short Gastrulation Gene (SOG)

<400> SEQUENCE: 2

```
Met Ala Asn Lys Leu Arg Lys Ser Asn Ala Ile Glu Trp Ala Thr Ala
1               5                   10                  15

Thr Gly Thr Val Pro Leu Leu Glu Arg Ser Cys Cys His Ser Glu Asp
            20                  25                  30

Ala Ala Leu Glu Pro Gln Ala Ser Lys Thr Ser His Arg Glu Gln Ala
        35                  40                  45

Pro Ile Leu Arg His Leu Ser Gln Leu Ser His Leu Leu Ile Ile Ala
    50                  55                  60

Gly Leu Leu Ile Val Cys Leu Ala Gly Val Thr Glu Gly Arg Arg His
65                  70                  75                  80

Ala Pro Leu Met Phe Glu Glu Ser Asp Thr Gly Arg Arg Ser Asn Arg
                85                  90                  95

Pro Ala Val Thr Glu Cys Gln Phe Gly Lys Val Leu Arg Glu Leu Gly
            100                 105                 110

Ser Thr Trp Tyr Ala Asp Leu Gly Pro Pro Phe Gly Val Met Tyr Cys
        115                 120                 125

Ile Lys Cys Glu Cys Val Ala Ile Pro Lys Lys Arg Arg Ile Val Ala
    130                 135                 140

Arg Val Gln Cys Arg Asn Ile Lys Asn Glu Cys Pro Pro Ala Lys Cys
145                 150                 155                 160
```

```
Asp Asp Pro Ile Ser Leu Pro Gly Lys Cys Cys Lys Thr Cys Pro Gly
            165                 170                 175

Asp Arg Asn Asp Thr Asp Val Ala Leu Asp Val Pro Val Pro Asn Glu
            180                 185                 190

Glu Glu Glu Arg Asn Met Lys His Tyr Ala Ala Leu Leu Thr Gly Arg
            195                 200                 205

Thr Ser Tyr Phe Leu Lys Gly Glu Glu Met Lys Ser Met Tyr Thr Thr
        210                 215                 220

Tyr Asn Pro Gln Asn Val Val Ala Thr Ala Arg Phe Leu Phe His Lys
225                 230                 235                 240

Lys Asn Leu Tyr Tyr Ser Phe Tyr Thr Ser Ser Arg Ile Gly Arg Pro
                245                 250                 255

Arg Ala Ile Gln Phe Val Asp Asp Ala Gly Val Ile Leu Glu His
            260                 265                 270

Gln Leu Glu Thr Thr Leu Ala Gly Thr Leu Ser Val Tyr Gln Asn Ala
            275                 280                 285

Thr Gly Lys Ile
        290

<210> SEQ ID NO 3
<211> LENGTH: 978
<212> TYPE: DNA
<213> ORGANISM: Drosophila Short Gastrulation Gene (SOG)

<400> SEQUENCE: 3
atggccaaca agctgaggaa atcgaacgcc atcgaatggg ccacggccac cggcacagta      60
ccgctcctgc aaaggagctg ctgccacagc gaggacgccg cactggagcc caagcgagc     120
aaaaccagcc atagagaaca agccccatc ctgcgccacc tgagccaact gagccacctg     180
ctcatcatcg ccggactgct gatcgtctgc ttggcgggcg tgacggaggg ccgccggcat     240
cgcccgctca tgttcgagga gtccgacacg ggcaggcggt ccaaccgacc agcggtcacc     300
gaatgccagt tggcaaagt tttgcgcgaa ttggggtcca cctggtatgc ggatttgggt     360
ccaccctttcg gagttatgta ctgcatcaag tgtgaatgtg tggcgatacc caagaagcgg     420
cgcatcgttg cacgcgtcca gtgtgcgaat atcaaaaacg agtgcccgcc ggccaaatgc     480
gatgatccca tctcgttgcc cggaaaatgc tgcaagacct gtcccggcga tcgaaacgat     540
acggatgtag ccttggatgt gcccgtgccc aatgaagagg aagagcgcaa catgaaacat     600
tacgctgcgt tgctaacggg ccgcacctcc tatttcctca agggtgagga aatgaagtcc     660
atgtacacca cctacaatcc gcagaatgtg gtggccaccg cccgtttcct gttccacaag     720
aagaatctat actactcctt ctacacctca tcgcgaatcg gtcgtccgcg tgccattcaa     780
ttcgttgatg atgcgggtgt aatcctggag gagcatcaac tggagaccac cttggcgggc     840
actctcagtg tctatcagaa tgccacgggc aagatcggcc gcggctcgag ggtacctcta     900
gaggatcttt gtgaaggaac cttacttctg tggtgtgaca taattggaca aactacctac     960
agagatttaa agctctaa                                                    978

<210> SEQ ID NO 4
<211> LENGTH: 325
<212> TYPE: PRT
<213> ORGANISM: Drosophila Short Gastrulation Gene (SOG)

<400> SEQUENCE: 4

Met Ala Asn Lys Leu Arg Lys Ser Asn Ala Ile Glu Trp Ala Thr Ala
```

```
            1               5                  10                 15
      Thr Gly Thr Val Pro Leu Leu Glu Arg Ser Cys Cys His Ser Glu Asp
                       20                  25                  30

Ala Ala Leu Glu Pro Gln Ala Ser Lys Thr Ser His Arg Glu Gln Ala
                       35                  40                  45

Pro Ile Leu Arg His Leu Ser Gln Leu Ser His Leu Leu Ile Ile Ala
                       50                  55                  60

Gly Leu Leu Ile Val Cys Leu Ala Gly Val Thr Glu Gly Arg Arg His
      65                  70                  75                  80

Ala Pro Leu Met Phe Glu Glu Ser Asp Thr Gly Arg Arg Ser Asn Arg
                       85                  90                  95

Pro Ala Val Thr Glu Cys Gln Phe Gly Lys Val Leu Arg Glu Leu Gly
                      100                 105                 110

Ser Thr Trp Tyr Ala Asp Leu Gly Pro Pro Phe Gly Val Met Tyr Cys
                      115                 120                 125

Ile Lys Cys Glu Cys Val Ala Ile Pro Lys Lys Arg Arg Ile Val Ala
                      130                 135                 140

Arg Val Gln Cys Arg Asn Ile Lys Asn Glu Cys Pro Pro Ala Lys Cys
      145                 150                 155                 160

Asp Asp Pro Ile Ser Leu Pro Gly Lys Cys Cys Lys Thr Cys Pro Gly
                      165                 170                 175

Asp Arg Asn Asp Thr Asp Val Ala Leu Asp Val Pro Val Pro Asn Glu
                      180                 185                 190

Glu Glu Glu Arg Asn Met Lys His Tyr Ala Ala Leu Leu Thr Gly Arg
                      195                 200                 205

Thr Ser Tyr Phe Leu Lys Gly Glu Glu Met Lys Ser Met Tyr Thr Thr
      210                 215                 220

Tyr Asn Pro Gln Asn Val Val Ala Thr Ala Arg Phe Leu Phe His Lys
      225                 230                 235                 240

Lys Asn Leu Tyr Tyr Ser Phe Tyr Thr Ser Ser Arg Ile Gly Arg Pro
                      245                 250                 255

Arg Ala Ile Gln Phe Val Asp Asp Ala Gly Val Ile Leu Glu Glu His
                      260                 265                 270

Gln Leu Glu Thr Thr Leu Ala Gly Thr Leu Ser Val Tyr Gln Asn Ala
                      275                 280                 285

Thr Gly Lys Ile Gly Arg Gly Ser Arg Val Pro Leu Glu Asp Leu Cys
                      290                 295                 300

Glu Gly Thr Leu Leu Leu Trp Cys Asp Ile Ile Gly Asn Thr Thr Tyr
      305                 310                 315                 320

Arg Asp Leu Lys Leu
                      325

<210> SEQ ID NO 5
<211> LENGTH: 978
<212> TYPE: DNA
<213> ORGANISM: Drosophila Short Gastrulation Gene (SOG)

<400> SEQUENCE: 5
atggccaaca agctgaggaa atcgaacgcc atcgaatggg ccacggccac cggcacagta      60
ccgctcctgg aaaggagctg ctgccacagc gaggacgccg cactggagcc caagcgagc     120 aaaaccagcc atagagaaca agcccccatc ctgcgccacc tgagccaact gagccacctg     180
ctcatcatcg ccggactgct gatcgtctgc ttggcgggcg tgacggaggg ccgccggcat     240
gcgccgctca tgttcgagga gtccgacacg ggcaggcggt ccaaccgacc agcggtcacc     300
```

```
gaatgccagt tggcaaagt tttgcgcgaa ttggggtcca cgcagtatgc ggatttgggt    360
ccacccttcg gagttatgta ctgcatcaag tgtgaatgtg tggcgatacc aagaagcgg    420 cgcatcgttg cacgcgtcca gtgtcgcaat atcaaaaacg agtgcccgcc ggccaaatgc    480
gatgatccca tctcgttgcc cggaaaatgc tgcaagacct gtcccggcga tcgaaacgat    540
acggatgtag ccttggatgt gcccgtgccc aatgaagagg aagagcgcaa catgaaacat    600
tacgctgcgt tgctaacggg ccgcacctcc tatttcctca agggtgagga aatgaagtcc    660
atgtacacca cctacaatcc gcagaatgtg gtggccaccg cccgtttcct gttccacaag    720
aagaatctat actactcctt ctacacctca tcgcgaatcg gtcgtccgcg tgccattcaa    780
ttcgttgatg atgcgggtgt aatcctggag gagcatcaac tggagaccac cttggcgggc    840
actctcagtg tctatcagaa tgccacgggc aagatcggcc gcggctcgag ggtacctcta    900
gaggatcttt gtgaaggaac cttacttctg tggtgtgaca taattggaca aactacctac    960
agagatttaa agctctaa                                                  978

<210> SEQ ID NO 6
<211> LENGTH: 325
<212> TYPE: PRT
<213> ORGANISM: Drosophila Short Gastrulation Gene (SOG)

<400> SEQUENCE: 6

Met Ala Asn Lys Leu Arg Lys Ser Asn Ala Ile Glu Trp Ala Thr Ala
 1               5                  10                  15

Thr Gly Thr Val Pro Leu Leu Glu Arg Ser Cys Cys His Ser Glu Asp
            20                  25                  30

Ala Ala Leu Glu Pro Gln Ala Ser Lys Thr Ser His Arg Glu Gln Ala
        35                  40                  45

Pro Ile Leu Arg His Leu Ser Gln Leu Ser His Leu Leu Ile Ile Ala
    50                  55                  60

Gly Leu Leu Ile Val Cys Leu Ala Gly Val Thr Glu Gly Arg Arg His
65                  70                  75                  80

Ala Pro Leu Met Phe Glu Glu Ser Asp Thr Gly Arg Arg Ser Asn Arg
                85                  90                  95

Pro Ala Val Thr Glu Cys Gln Phe Gly Lys Val Leu Arg Glu Leu Gly
            100                 105                 110

Ser Thr Ala Tyr Ala Asp Leu Gly Pro Pro Phe Gly Val Met Tyr Cys
        115                 120                 125

Ile Lys Cys Glu Cys Val Ala Ile Pro Lys Lys Arg Arg Ile Val Ala
    130                 135                 140

Arg Val Gln Cys Arg Asn Ile Lys Asn Glu Cys Pro Pro Ala Lys Cys
145                 150                 155                 160

Asp Asp Pro Ile Ser Leu Pro Gly Lys Cys Cys Lys Thr Cys Pro Gly
                165                 170                 175

Asp Arg Asn Asp Thr Asp Val Ala Leu Asp Val Pro Asp Pro Asn Glu
            180                 185                 190

Glu Glu Glu Arg Asn Met Lys His Tyr Ala Ala Leu Leu Thr Gly Arg
        195                 200                 205

Thr Ser Tyr Phe Leu Lys Gly Glu Glu Met Lys Ser Met Tyr Thr Thr
    210                 215                 220

Tyr Asn Pro Gln Asn Val Val Ala Thr Ala Arg Phe Leu Phe His Lys
225                 230                 235                 240

Lys Asn Leu Tyr Tyr Ser Phe Tyr Thr Ser Ser Arg Ile Gly Arg Pro
```

```
                   245                 250                 255
Arg Ala Ile Gln Phe Val Asp Asp Ala Gly Val Ile Leu Glu Glu His
                260                 265                 270

Lys Leu Glu Thr Thr Leu Ala Gly Thr Leu Ser Val Tyr Gln Asn Ala
            275                 280                 285

Thr Gly Lys Ile Gly Arg Gly Ser Arg Val Pro Leu Glu Asp Leu Cys
        290                 295                 300

Glu Gly Thr Leu Leu Leu Trp Cys Asp Ile Ile Gly Asn Thr Thr Tyr
305                 310                 315                 320

Arg Asp Leu Lys Leu
                325

<210> SEQ ID NO 7
<211> LENGTH: 1041
<212> TYPE: DNA
<213> ORGANISM: Drosophila Short Gastrulation Gene (SOG)

<400> SEQUENCE: 7
atggccaaca agctgaggaa atcgaacgcc atcgaatggg ccacggccac cggcacagta      60
ccgctcctgg aaaggagctg ctgccacagc gaggacgccg cactggagcc caagcgagc     120
aaaaccagcc atagaaaca gcccccatc ctgcgccacc tgagccaact gagccacctg      180
ctcatcatcg ccggactgct gatcgtctgc ttggcgggcg tgacggaggg ccgccggcat    240
gcgccgctca tgttcgagga gtccgacacg ggcaggcggt ccaaccgacc agcggtcacc    300
gaatgccagt ttggcaaagt tttgcgcgaa ttggggtcca cctggtatgc ggatttgggt    360
ccacccttcg gagttatgta ctgcatcaag tgtgaatgtg tggcgatacc caagaagcgg    420
cgcatcgttg cacgcgtcca gtgtcgcaat atcaaaaacg agtgcccgcc ggccaaatgc    480
gatgatccca tctcgttgcc cggaaaatgc tgcaagacct gtcccggcga tcgaaacgat    540
acggatgtag ccttggatgt gcccgtgccc aatgaagagg aagagcgcaa catgaaacat    600
tacgctgcgt tgctaacggg cgcgaccctcc tatttcctca agggtgagga aatgaagtcc    660
atgtacacca cctacaatcc gcagaatgtg gtggccaccg cccgtttcct gttccacaag    720
aagaatctat actactcctt ctacacctca tcgcgaatcg gtcgtccgcg tgccattcaa    780
ttcgttgatg atgcgggtgt aatcctggag gagcatcaac tggagaccac cttggcgggc    840
actctcagtg tctatcagaa tgccacgggc aagatcggcc gcggctcgag gcagcgcggc    900
cgcatctttt acccatacga tgttcctgac tatgcgggct atccctatga cgtcccggac    960
tatgcaggat cctatccata tgacgttcca gattacgctg ctcagtgcgg ccgcgattat   1020
agggacgacg acgacaaatc a                                             1041

<210> SEQ ID NO 8
<211> LENGTH: 346
<212> TYPE: PRT
<213> ORGANISM: Drosophila Short Gastrulation Gene (SOG)

<400> SEQUENCE: 8

Met Ala Asn Lys Leu Arg Lys Ser Asn Ala Ile Glu Trp Ala Thr Ala
1               5                  10                  15

Thr Gly Thr Val Pro Leu Leu Glu Arg Ser Cys Cys His Ser Glu Asp
            20                  25                  30

Ala Ala Leu Glu Pro Gln Ala Ser Lys Thr Ser His Arg Glu Gln Ala
        35                  40                  45

Pro Ile Leu Arg His Leu Ser Gln Leu Ser His Leu Leu Ile Ile Ala
```

```
                50                    55                    60
Gly Leu Leu Ile Val Cys Leu Ala Gly Val Thr Glu Gly Arg Arg His
 65                  70                  75                  80

Ala Pro Leu Met Phe Glu Glu Ser Asp Thr Gly Arg Arg Ser Met Arg
                 85                  90                  95

Pro Ala Val Thr Glu Cys Gln Phe Gly Lys Val Leu Arg Glu Leu Gly
            100                 105                 110

Ser Thr Trp Tyr Ala Asp Leu Gly Pro Pro Phe Gly Val Met Tyr Cys
            115                 120                 125

Ile Lys Cys Glu Cys Val Ala Ile Pro Lys Lys Arg Arg Ile Val Ala
130                 135                 140

Arg Val Gln Cys Arg Asn Ile Lys Asn Glu Cys Pro Pro Ala Lys Cys
145                 150                 155                 160

Asp Asp Pro Ile Ser Leu Pro Gly Lys Cys Cys Lys Thr Cys Pro Gly
            165                 170                 175

Asp Arg Asn Asp Thr Asp Val Ala Leu Asp Val Pro Val Pro Asn Glu
            180                 185                 190

Glu Glu Glu Arg Asn Met Lys His Tyr Ala Ala Leu Leu Thr Gly Arg
            195                 200                 205

Thr Ser Tyr Phe Leu Lys Gly Glu Glu Met Lys Ser Met Tyr Thr Thr
210                 215                 220

Tyr Asn Pro Gln Asn Val Val Ala Thr Ala Arg Phe Leu Phe His Lys
225                 230                 235                 240

Lys Asn Leu Tyr Tyr Ser Phe Tyr Thr Ser Arg Ile Gly Arg Pro
            245                 250                 255

Arg Ala Ile Gln Phe Val Asp Asp Ala Gly Val Ile Leu Glu Glu His
            260                 265                 270

Gln Leu Glu Thr Thr Leu Ala Gly Thr Leu Ser Val Tyr Gln Met Ala
            275                 280                 285

Thr Gly Lys Ile Gly Arg Gly Ser Arg Asn Arg Gly Arg Ile Phe Tyr
            290                 295                 300

Pro Tyr Asp Val Pro Asp Tyr Ala Gly Tyr Pro Tyr Asp Val Pro Asp
305                 310                 315                 320

Tyr Ala Gly Ser Tyr Pro Tyr Asp Val Pro Asp Tyr Ala Ala Asn Cys
            325                 330                 335

Gly Arg Asp Tyr Lys Asp Asp Asp Lys
            340                 345

<210> SEQ ID NO 9
<211> LENGTH: 213
<212> TYPE: PRT
<213> ORGANISM: Drosophila Short Gastrulation Gene (SOG)

<400> SEQUENCE: 9

Met Asp His Ser Gln Cys Leu Val Thr Ile Tyr Ala Leu Met Val Phe
 1               5                  10                  15

Leu Gly Leu Arg Ile Asp Gln Gly Gly Cys Gln His Tyr Leu His Ile
             20                  25                  30

Arg Pro Ala Pro Ser Glu Asn Leu Pro Leu Val Asp Leu Ile Glu His
         35                  40                  45

Pro Asp Pro Ile Tyr Asp Pro Lys Glu Lys Asp Glu Leu Asn Glu Thr
     50                  55                  60

Leu Leu Arg Thr Leu Met Val Gly His Phe Asp Pro Ile Leu Pro Glu
 65                  70                  75                  80
```

```
Glu Arg Leu Gly Val Glu Asp Leu Gly Glu Leu Asp Leu Leu Leu Arg
                85                  90                  95
Gln Lys Pro Ser Gly Ala Met Pro Ala Glu Ile Lys Gly Leu Glu Phe
            100                 105                 110
Tyr Glu Gly Leu Gln Ser Lys Lys His Arg Leu Ser Lys Lys Leu Arg
        115                 120                 125
Arg Lys Leu Gln Met Trp Leu Trp Ser Gln Thr Phe Cys Pro Val Leu
    130                 135                 140
Tyr Thr Trp Asn Asp Leu Gly Arg Tyr Val Lys Val Gly Ser Cys Tyr
145                 150                 155                 160
Ser Lys Arg Ser Cys Ser Val Pro Glu Gly Met Val Cys Lys Ala Ala
                165                 170                 175
Lys Ser Met His Leu Thr Ile Leu Arg Trp Arg Cys Gln Arg Arg Val
            180                 185                 190
Gln Gln Lys Cys Ala Trp Ile Thr Ile Gln Tyr Pro Val Ile Ser Glu
        195                 200                 205
Cys Lys Cys Ser Cys
    210

<210> SEQ ID NO 10
<211> LENGTH: 53
<212> TYPE: PRT
<213> ORGANISM: Drosophila Short Gastrulation Gene (SOG)

<400> SEQUENCE: 10

Val Asp Leu Ile Glu His Pro Asp Pro Ile Tyr Asp Pro Lys Glu Lys
1               5                   10                  15
Asp Leu Asn Glu Thr Leu Leu Arg Thr Leu Met Val Gly His Phe Asp
            20                  25                  30
Pro Ile Leu Pro Glu Glu Arg Leu Gly Val Glu Asp Leu Gly Glu Leu
        35                  40                  45
Asp Leu Leu Leu Arg
    50

<210> SEQ ID NO 11
<211> LENGTH: 4892
<212> TYPE: DNA
<213> ORGANISM: Drosophila Short Gastrulation Gene (SOG)

<400> SEQUENCE: 11
atattagatg acatgcata ataattattc atgtaactat gtgattttca ttttacacga      60
ggtgtcagtc agaatttaaa attcttaaaa attgcaatca cggtctattg tacatattta     120
tgtatgcgat ctcattatta ttattattat tatttgataa tatattagca gctgttcaaa     180
tcatcaacaa gtataaaatt gaaaatgtta aaaattgaag cagtcttggg tttgcctgca     240
acatgttgct gccgatcgtt agatgttgct gctgcatgtt gccgctgcat gttgccgttg     300
catgttgccg ccgtttggca actttataaa cacggagcgg attcagtcgt tcaggttcag     360
tctctcttga attgcgtggg attgcacatc ggtcgttcgg cttttttgggt tcggcattta    420 gagagatacg atacgatccg atacgatccg atccagtaca aaaatcaaat tcaaaccgca     480
ctcccgatcc ggtcgccatc atatacacgg cggctcgcac cgcagctatc tagtagataa     540
aaagtcgccg agaacgcagt acgcatatag cgaaacgcca aaaaataaaa aaaaaagtc     600 gcgttgtcgt aatccctcct catacgagat cgactctatt ttccagagca agctaaacac     660
actagtgcta aaccataact atatatctaa ctaaggaaaa caaagtctcg aaactgaaaa     720
```

```
cgaaaagcgc aaatttatgc agccgctaaa taaaaacaga aaccaaaaca taaaacacac    780
tatacaaatc atacaaaaca aaaacagcga atcaaatagt ataaaaaaaa aataaataaa    840
tgaggaataa aaaaacaggc aaatagaata aatccaataa atcggcgcgc gaaactccgc    900
tgtgttatct aatctgcaag agaagtacaa gaatcgggta tagaatcggc tctatactat    960
atctatacac ctgatatatc tatatccatt gtgtgtgcca gtgtgtgcgt ggcgaccttt   1020
gtttttatat atttttttgtt gttgttcata ctgtgaaacg tgcttttttac aagccggtcg   1080 ttcaaaatac aaaatactac aaatcaaatc aaatcatata cacatacata tcagtaaaaa   1140
caaaacaaaa aacacataaa catggccaac aagctgagga atcgaacgc catcgaatgg    1200 gccacggcca ccggcacagt accgctcctg gaaaggagct gctgccacag cgaggacgcc   1260
gcactggagc cccaagcgag caaaaccagc catagagaac aagcccccat cctgcgccac   1320
ctgagccaac tgagccacct gctcatcatc gccggactgc tgatcgtctg cttggcgggc   1380
gtgacggagg gccgccggca tcgcccgctc atgttcgagg agtccgacac gggcaggcgg   1440
tccaaccgac cagcggtcac cgaatgccag tttggcaaag ttttgcgcga attggggtcc   1500
acctggtatg cggatttggg tccacccttc ggagttatgt actgcatcaa gtgtgaatgt   1560
gtggcgatac ccaagaagcg cgcatcgtt gcacgcgtcc agtgtcgcaa tatcaaaaac    1620
gagtgcccgc cggccaaatg cgatgatccc atctcgttgc ccggaaaatg ctgcaagacc   1680
tgtcccggcg atcgaaacga tacggatgta gccttggatg tgcccgtgcc caatgaagag   1740
gaagagcgca acatgaaaca ttacgctgcg ttggtaacgg gccgcaccte ctatttccte   1800 aagggtgagg aaatgaagtc catgtacacc acctacaatc cgcagaatgt ggtggccacc   1860
gcccgtttcc tgttccacaa gaagaatcta tactactcct tctacacctc atcgcgaatc   1920
ggtcgtccgc gtgccattca attcgttgat gatgcgggtg taatcctgga ggagcatcaa   1980
ctggagacca ccttggcggg cactctcagt gtctatcaga atgccacggg caagatctgc   2040
ggtgtctggc gacgagttcc acgtgattac aagcgcatcc tggcggacga tgctctccat   2100
gttgtcctcc tctggggcaa caaacagcag gccgagttgg ctctggccgg aaaggtggcc   2160
aaatacacgg ccctgcagac ggagttgttc agttcgctac tggaggcacc acttcccgat   2220
ggcaaaacgg atccccagct ggccggagcc ggtggcacag cgatcgtgtc caccagcagc   2280
ggtgccgcct catcgatgca tctcaccctg gtcttcaatg gtgtctttgg tgccgaggag   2340
tacgccgatg cagcactgag tgtgaaaatt gagctggcag aacggaagga ggtgatcttc   2400
gatgagattc cacgtgtgcg caaaccctct gccgagatca atgtcctgga gctgtcgtcg   2460
cccatttcca tacagaatct tcgactgatg tcgcgtggca aactcctgct gaccgtggag   2520
tccaagaagt acccacatct gcgcatccag ggacacatcg tgacccgagc cagctgcgaa   2580
atcttccaga ccctgctggc gccgcacagt gccgaatcct cgaccaagag cagcggtttg   2640
gcgtgggtct acttgaacac cgatggatct ctggcctaca catcgaaac ggagcacgtg    2700 aacacccggg ataggcccaa catcagtttg attgaggagc agggcaagcg gaaggccaag   2760
ctggaggatc tgacgccgag cttcaacttc aaccaggcca ttggtagtgt ggagaagttg   2820
ggtcccaagg tcctcgagtc gctgtatgcc ggcgaactgg gcgttaatgt ggccaccgag   2880
catgagacga gcctgatccg tggccgccta gtgcccgtc cagtggccga tgctcggac     2940 tcggcggaac ccattctgct gaagcgacag gagcacacgg atgcacagaa tccacatgcc   3000
gtcggcatgg cctggatgtc cattgacaac gagtgcaatc tgcactacga ggtgacgctc   3060
aacggtgtgc ccgcccagga tctgcagctg tatctggagg agaagcccat cgaggcgatt   3120
```

-continued

```
ggagcgccag tgacgaggaa attgctcgag gaattcaacg gctcctatct ggaaggcttc    3180
ttcctcagca tgccatccgc cgaactgatc aagctggaga tgagcgtctg ctatctggag    3240
gtccattcca agcactccaa acagcttctg ctgcgcggca aactgaagag caccaaggtg    3300
ccgggtcact gcttccccgt ctatacggac aacaatgttc ccgtgcctgg cgaccacaat    3360
gataaccatt tggtgaacgg agagaccaag tgctttcact ccggacgctt ctacaacgaa    3420
tcggagcatt ggcgcagtgc ccaggattcc tgtcagatgt gcgcctgttt gcgtggccaa    3480
cacagttgcg aggtcatcaa gtgtccgcct ctcaagtgca agtccacgga gcaactgctt    3540
cagagtgatg gtgaatgctg tcccagctgt gtgcccaaga aggaggccgc cgactattca    3600
gcgcaatcct cgccagccac caatgccacc gatttgctgc aacagcgacg cggctgcgcg    3660
ctgggcgagc agttccatcc cgccggtgcc agttggcatc cattcctgcc gcccaatggc    3720
ttcgatacct gcaccacctg cagctgcgat cccctgaccc tcgagattcg ctgtccccgg    3780
ctcgtctgcc cgccgttgca gtgcagcgag aagttggcct atcgtccaga caagaaggca    3840
tgctgcaaga tctgtccgga gggcaagcag agcagttcca atggacacaa gacgacgccg    3900
aacaatccca atgtgctgca ggatcaggcc atgcagcgat cgccgagtca cagtgccgag    3960
gaggttctgg ccaacggcgg atgcaaggtg gtcaacaagg tgtacgagaa cggccaggag    4020
tggcatccga tcctgatgtc ccacggcgag cagaagtgca tcaagtgccg ctgcaaggac    4080
tccaaggtga actgcgatgc caagcgctgc tcccgctcca cgtgccagca gcagacacgc    4140
gtgaccagca acggcgtct gttcgagaaa ccggacgcag ctgctccggc catcgatgac    4200
ttctgctcca cccactgccg gagatcgagg cgccaccaca agaggcagcc gcatcatcag    4260
cagcgatcct ccagctgagc ggctccacgt gacggatggg atcccaatcc agtatcagat    4320
ccttggcggc aggggagcga accaatcact cactcactca ccaccactca gtgtactcag    4380
tgtgcaccac ccaaacacac acacacacac acacacacaa ccacacaaca ctcacacccca    4440 catctacaca gacacacaga cagccacaaa agcgaacgcg cacacagact tgtgcaagga    4500
gttgcataga tcgttgttgc tatcttatca tgtggcagca atgagaactt gtattatata    4560
tatgaatcac ggaggagaaa acgtaggaga gaaatctcac aaaaaatata tatatcttat    4620
ggaggaaaac ggtagtaata gagagagaga gagagggaag gagagagtct aatgagatcc    4680
ttggaaaagg acattaaaac cagtgcagtt tgctttaaat tctccagcgc agaattttct    4740
attgaaagca ttttctgaat ttcttttcgc agttaccccca cccgtgtaac ccaatcccct    4800
cccctcccca accaacaaac acccaaaaaa aaaaactaaa acattaaaa tacaatttta    4860 atttattaca aaacaaaaac aaaaaaaaa aa                                    4892
```

<210> SEQ ID NO 12
<211> LENGTH: 1038
<212> TYPE: PRT
<213> ORGANISM: Drosophila Short Gastrulation Gene (SOG)

<400> SEQUENCE: 12

```
Met Ala Asn Lys Leu Arg Lys Ser Asn Ala Ile Glu Trp Ala Thr Ala
1               5                   10                  15

Thr Gly Thr Val Pro Leu Leu Glu Arg Ser Cys Cys His Ser Glu Asp
            20                  25                  30

Ala Ala Leu Glu Pro Gln Ala Ser Lys Thr Ser His Arg Glu Gln Ala
        35                  40                  45

Pro Ile Leu Arg His Leu Ser Gln Leu Ser His Leu Leu Ile Ile Ala
```

```
         50                  55                  60
Gly Leu Leu Ile Val Cys Leu Ala Gly Val Thr Glu Gly Arg Arg His
 65                  70                  75                  80

Ala Pro Leu Met Phe Glu Glu Ser Asp Thr Gly Arg Arg Ser Asn Arg
                 85                  90                  95

Pro Ala Val Thr Glu Cys Gln Phe Gly Lys Val Leu Arg Glu Leu Gly
            100                 105                 110

Ser Thr Trp Tyr Ala Asp Leu Gly Pro Pro Phe Gly Val Met Tyr Cys
        115                 120                 125

Ile Lys Cys Glu Cys Val Ala Ile Pro Lys Lys Arg Arg Ile Val Ala
    130                 135                 140

Arg Val Gln Cys Arg Asn Ile Lys Asn Glu Cys Pro Pro Ala Lys Cys
145                 150                 155                 160

Asp Asp Pro Ile Ser Leu Pro Gly Lys Cys Cys Lys Thr Cys Pro Gly
                165                 170                 175

Asp Arg Asn Asp Thr Asp Val Ala Leu Asp Val Pro Val Pro Asn Glu
            180                 185                 190

Glu Glu Glu Arg Asn Met Lys His Tyr Ala Ala Leu Leu Thr Gly Arg
        195                 200                 205

Thr Ser Tyr Phe Leu Lys Gly Glu Glu Met Lys Ser Met Tyr Thr Thr
    210                 215                 220

Tyr Asn Pro Gln Asn Val Val Ala Thr Ala Arg Phe Leu Phe His Lys
225                 230                 235                 240

Lys Asn Leu Tyr Tyr Ser Phe Tyr Thr Ser Arg Ile Gly Arg Pro
                245                 250                 255

Arg Ala Ile Gln Phe Val Asp Asp Ala Gly Asx Ile Leu Glu Glu His
            260                 265                 270

Gln Leu Glu Thr Thr Leu Ala Gly Thr Leu Ser Val Tyr Gln Asn Ala
        275                 280                 285

Thr Gly Lys Ile Cys Gly Val Trp Arg Arg Val Pro Arg Asp Tyr Lys
            290                 295                 300

Arg Ile Leu Arg Asp Asp Arg Leu His Val Val Leu Leu Trp Gly Asn
305                 310                 315                 320

Lys Gln Gln Ala Glu Leu Ala Leu Ala Gly Lys Val Ala Lys Tyr Thr
                325                 330                 335

Ala Leu Gln Thr Glu Leu Phe Ser Ser Leu Leu Glu Ala Pro Leu Pro
            340                 345                 350

Asp Gly Lys Thr Asp Pro Gln Leu Ala Gly Ala Gly Thr Ala Ile
        355                 360                 365

Val Ser Thr Ser Ser Gly Ala Ala Ser Ser Met His Leu Thr Leu Val
    370                 375                 380

Phe Asn Gly Val Phe Gly Ala Glu Glu Tyr Ala Asp Ala Ala Leu Ser
385                 390                 395                 400

Val Lys Ile Glu Leu Ala Glu Arg Lys Glu Val Ile Phe Asp Glu Ile
                405                 410                 415

Pro Arg Val Arg Lys Pro Ser Ala Glu Ile Asn Val Leu Glu Leu Ser
            420                 425                 430

Ser Pro Ile Ser Ile Gln Asn Leu Arg Leu Met Ser Arg Gly Lys Leu
        435                 440                 445

Leu Leu Thr Val Glu Ser Lys Lys Tyr Pro His Leu Arg Ile Gln Gly
    450                 455                 460

His Ile Val Thr Arg Ala Ser Cys Glu Ile Phe Gln Thr Leu Leu Ala
465                 470                 475                 480
```

```
Pro His Ser Ala Glu Ser Ser Thr Lys Ser Gly Leu Ala Trp Val
            485                 490                 495

Tyr Leu Asn Thr Asp Gly Ser Leu Ala Tyr Asn Ile Glu Thr Glu His
            500                 505                 510

Val Asn Thr Arg Asp Arg Pro Asn Ile Ser Leu Ile Glu Glu Gln Gly
            515                 520                 525

Lys Arg Lys Ala Lys Leu Glu Asp Leu Thr Pro Ser Phe Asn Phe Asn
            530                 535                 540

Gln Ala Ile Gly Ser Val Glu Lys Leu Gly Pro Lys Val Leu Glu Ser
545                 550                 555                 560

Leu Tyr Ala Gly Glu Leu Gly Val Asn Val Ala Thr Glu His Glu Thr
                565                 570                 575

Ser Leu Ile Arg Gly Arg Leu Val Pro Arg Pro Val Ala Asp Ala Arg
                580                 585                 590

Asp Ser Ala Glu Pro Ile Leu Leu Lys Arg Gln Glu His Thr Asp Ala
            595                 600                 605

Gln Asn Pro His Ala Val Gly Met Ala Trp Met Ser Ile Asp Asn Glu
            610                 615                 620

Cys Asn Leu His Tyr Glu Val Thr Leu Asn Gly Val Pro Ala Gln Asp
625                 630                 635                 640

Leu Gln Leu Tyr Leu Glu Glu Lys Pro Ile Glu Ala Ile Gly Ala Pro
                645                 650                 655

Val Thr Arg Lys Leu Leu Glu Glu Phe Asn Gly Ser Tyr Leu Glu Gly
                660                 665                 670

Phe Phe Leu Ser Met Pro Ser Ala Glu Leu Ile Lys Leu Glu Met Ser
            675                 680                 685

Val Cys Tyr Leu Glu Val His Ser Lys Met Ser Lys Cys Leu Leu Leu
            690                 695                 700

Arg Gly Lys Leu Lys Ser Thr Lys Val Pro Gly His Cys Phe Pro Val
705                 710                 715                 720

Tyr Thr Asp Asn Asn Val Pro Val Pro Gly Asp His Asn Asp Asn His
                725                 730                 735

Leu Val Asn Gly Glu Thr Lys Cys Phe His Ser Gly Arg Phe Tyr Asn
                740                 745                 750

Glu Ser Glu Gln Trp Arg Ser Ala Gln Asp Ser Cys Gln Met Cys Ala
            755                 760                 765

Cys Leu Arg Gly Gln Ser Ser Cys Glu Val Ile Lys Cys Pro Ala Leu
            770                 775                 780

Lys Cys Lys Ser Thr Glu Gln Leu Leu Gln Arg Asp Gly Glu Cys Cys
785                 790                 795                 800

Pro Ser Cys Val Pro Lys Lys Glu Ala Ala Asp Tyr Ser Ala Gln Ser
                805                 810                 815

Ser Pro Ala Thr Asn Ala Thr Asp Leu Leu Gln Gln Arg Arg Gly Cys
                820                 825                 830

Arg Leu Gly Glu Gln Phe His Pro Ala Gly Ala Ser Trp His Pro Phe
            835                 840                 845

Leu Pro Pro Asn Gly Phe Asp Thr Cys Thr Thr Cys Ser Cys Asp Pro
850                 855                 860

Leu Thr Leu Glu Ile Arg Cys Pro Arg Leu Val Cys Pro Pro Leu Gln
865                 870                 875                 880

Cys Ser Glu Lys Leu Ala Tyr Pro Pro Asp Lys Lys Ala Cys Cys Lys
                885                 890                 895
```

-continued

```
Ile Cys Pro Glu Gly Tyr Gln Ser Ser Ser Asn Gly His Lys Thr Thr
            900                 905                 910

Pro Asn Asn Pro Asn Val Leu Gln Asp Gln Ala Met Gln Arg Ser Pro
        915                 920                 925

Ser His Ser Ala Glu Glu Val Leu Ala Asn Gly Gly Cys Lys Val Val
        930                 935                 940

Asn Lys Val Tyr Glu Asn Gly Gln Glu Trp His Pro Ile Leu Met Ser
945                 950                 955                 960

His Gly Glu Gln Lys Cys Ile Lys Cys Arg Cys Lys Asp Ser Lys Val
                965                 970                 975

Asn Cys Asp Ala Lys Arg Cys Ser Arg Ser Thr Cys Gln Gln Gln Thr
            980                 985                 990

Arg Val Thr Ser Lys Arg Arg Leu Phe Glu Lys Pro Asp Ala Ala Ala
        995                 1000                1005

Pro Ala Ile Asp Glu Phe Cys Ser Thr Gln Cys Arg Arg Ser Arg
    1010                1015                1020

Arg His His Lys Arg Gln Pro His His Gln Gln Arg Ser Ser Ser
1025                1030                1035
```

PEPTIDE INHIBITOR OF TGF-β GROWTH FACTORS

This application is a Division of U.S. application Ser. No. 09/215,569 filed Dec. 16, 1998, which claims priority to U.S. Provisional 60/069,701 filed Dec. 16, 1997, both of which re incorporated herein by reference in their entirety.

BACKGROUND OF THE INVENTION

1. Field of the Invention

The invention relates to a peptide and homologues thereof which inhibit the activity of TGF-β family growth factors in vertebrates, as well as TGF-β-like growth factors in Drosophilia. Specifically, the invention relates to a highly potent fragment of the product of the Drosophilia short gastrulation gene (Sog).

2. History of the Related Art

During vertebrate development growth factors in the TGF-β superfamily control a number of events in tissue differentiation and morphogenesis. Included in the TGF-β superfamily are the bone morphogenic proteins, which promote the growth of new bone tissue and differentiation of osteoblasts. Examples of members of this family of BMPs are BMP-4 and BMP-7, which suppress neurogenesis during early embryonic development and are active in aspects of adult physiology.

BMP-4 has been highly conserved through evolution and has a functional and structural homologue in Drosophilia, known as Dpp. BMP-4 can substitute for Dpp in Drosophilia (Padgett, et al., *Proc. Natl. Acad. Sci. USA*, 90:2905-2909 (1993)) and Dpp is active in vertebrate tissues (Sampath, et al., *Proc. Natl. Acad. Sci. USA*, 90:6004-6008 (1993)). In vertebrates, chordin is a high affinity BMP-4 binding protein which inhibits BMP-4 and BMP-7 activity (Sasai, et al., *Cell*, 779-790 (1994)); in flies, the short gastrulation (Sog) protein inhibits Dpp activity (Francois, et al., *Genes & Dev.*, 8:2602-2616 (1994)). Again chordin and Sog are functional and structural homologues (Schmidt, et al., *Development*, 121: 4319-4328 (1995) and Francois, et al., *Cell*, 80:19-20 (1995)). In particular, Sog inhibits BMP-4 activity in vertebrates in a manner similar to chordin (Schmidt, et al., id.). It is highly probable that Sog inhibits the activity of other members of the TGF-β family such as BMP-7, which is also inhibited by chordin.

Abnormal activity on the part of BMP-4 has been linked to human cancer, including osteosarcoma and certain leukemias. Interestingly, over-expression of BMP-4 (which is potentiated by BMP-7) has also been shown to stimulate the onset of alopecia (male pattern baldness) in mice, perhaps due to an effect on hair follicle development. Control of such activity can have therapeutic benefit in these and other conditions related to abnormalities in the functioning of TGF-β family growth factors, especially on the part of BMP-4.

SUMMARY OF THE INVENTION

The invention provides a highly potent inhibitor of TGF-β growth factor activity, with particular impact on BMP-4. In particular, the invention identifies a fragment of the Drosophilia Sog protein which has an unexpectedly high level of Dpp inhibitory activity as compared to the intact, wild-type protein.

Based on the known homologies between Dpp and BMP-4, as well as between Sog and chordin, together with other supportive data discussed below, it is predictable that the Sog fragment of the invention (hereafter, "Super-Sog") functions as an inhibitor of BMP-4 and BMP-7 activity in vertebrates. Surprisingly, Super-Sog has a broader scope of activity than wild-type Sog in the sense that mutant phenotypes not produced by Sog inhibition of Dpp are produced in response to Super-Sog. This phenomenon suggests that Super-Sog is more potent than Sog and/or that it affects additional receptor-ligand interactions not affected by the wild-type protein, such as those mediated by activin, a vertebrate endocrine regulator whose Drosophilia homologue mediates wing development.

The invention therefore provides Super-Sog (SEQ ID NO:2; amino acids 1-292 of Sog) and active variants thereof. Such variants include SEQ ID NO:4, a recombinant Super-Sog peptide which includes 33 amino acids encoded by the pUAS expression vector; SEQ ID NO:6, a Super-Sog peptide which includes a mutation (W-A) in the CR-1 sequence; and SEQ ID NO:8, a Super-Sog peptide which terminates 5' of the CR-1 sequence. Such variants also include Super-Sog with 5' modifications, such as modifications to the Tolloid protease cleavage site, addition of other peptides and inclusion of additional 5' regions of Sog (e.g., CR-2).

The invention further provides pharmaceutical compositions of Super-Sog and methods for their use. Especially useful among the pharmaceutical compositions are those which are prepared so as to increase the bioavailability of Super-Sog in vivo by, for example, protecting the peptide against unintended proteolysis.

Methods for use of Super-Sog include its therapeutic use in arresting the development of male pattern baldness, assisting in the treatment of cancer (e.g., osteosarcomas) and inhibiting TGF-β growth factor (e.g., BMP-4, BMP-7 and activin) mediated suppression of neurogenesis to, for example, enhance the viability of fetal nervous tissue grafts in the treatment of neurodegenerative disorders such as Alzheimer's Disease, Parkinson's Disease and Huntington's Disease.

DESCRIPTION OF THE PREFERRED EMBODIMENTS

I

Structure and Activity of Super-Sog

The Sog coding sequence (Francois, et al., *Genes & Dev.*, 8:2602-2616 (1994)) contains 4 cysteine-rich repeat sequences (CR-1 through CR-4). The CR repeats are defined by a fixed spacing of 10 cysteine residues (excepting CR-4, which lacks the ninth cysteine) and share other many amino acids in common. CR-1 is located immediately after the putative transmembrane domain of the Sog protein, while CR-2 through CR-4 are located closer to the coding region for the carboxyl terminus of the protein.

Given their similarity in structure, it would be reasonably expected that any Dpp inhibitory activity conferred on the Sog protein by the CR repeats would be comparable in quality. It was therefore a surprise to find that a peptide encoded by CR-1 (Super-Sog; SEQ ID NO:1) has greater Dpp inhibitory activity in certain respects than wild-type Sog.

In particular, both Sog and Super-Sog inhibit Dpp-mediated activation of the *rhomboid* (rho) gene (which stimulates wing vein development in pupal Drosophilia). However, as between Super-Sog and Sog, only the former inhibits Dpp-mediated expression of the *spalt* gene which encodes a transcription factor that influences wing vein placement in an earlier stage of Drosophilia development (Example I). Thus, Super-Sog appears to be at least as potent, and broader in spectrum, a TGF-β family growth factor inhibitor than wild-type Sog.

II

Pharmaceutical Uses for Super-Sog

Given the apparent proficiency of Sog to inhibit the activity of TGF-β family growth factors (e.g., BMP-4 and BMP-7; collectively, "Target Factors") in vertebrates, Super-Sog should be useful in suppressing, for example, BMP-4 signalling in conditions where hyperactivity in such signalling is causative. The relatively small size of the Super-Sog peptide, coupled with its potency as compared to Sog, makes Super-Sog a particularly attractive compound for pharmaceutical use.

Clinically, Super-Sog will be useful in the same therapies which are or may be practiced with inhibitors of TGF-β activity, especially activity mediated by BMP-4 signalling. Thus, therapeutic uses for Super-Sog include, but are not limited to, stimulation of bone growth and repair through osteogenesis, inhibiting BMP-4 suppression of neurogenesis at the site of nervous tissue grafts (e.g., fetal tissue grafts in Huntington's patients), stimulating neurogenesis as a adjunct to therapy, of neurodegenerative disorders (e.g., in Huntington's, Parkinson's and Alzheimer's disease) and suppression of BMP-4 signalling of cancerous growth.

II

Methods for Manufacture of Super-Sog

Super-Sog is prepared as a purified peptide fragment from Sog (e.g., SEQ ID NO:2), expressed as a recombinant peptide using, for example, the coding sequences set forth in SEQ ID NOs:1, 3, 5 or 7, or synthesized chemically. Techniques for production of peptides according to each of these methods are well-known in the art and so will only be described briefly here.

In this respect, it will be appreciated by those of ordinary skill in the art that additions, substitutions and deletions of amino acids in the Super-Sog peptide sequences specifically described herein may be made without adversely altering the activity of the peptide. For example, a U-A substitution between the first two cysteines in CR-1 does not affect the activity of Super-Sog. Similarly, extending the length of Super-Sog 3' through the transmembrane and intracellular regions of Sog does not affect the activity of the peptide (although the increased length may decrease its bioavailability). Thus, in general, deletions and mutations made 3' to the CR-1 region in Super-Sog do not appear to adversely affect its activity.

Similarly, adding the CR-2 region or other constructs, such as a polyA sequence, to SuperSog 5' of the CR-1 region does not appear to adversely affect its activity. However, deletion of the entire peptide 5' of the CR-1 region negates the activity of Super-Sog. Thus, it appears that at least a portion of the SuperSog peptide 5' to the CR-1 region (between CR-1 and CR-2) is necessary to the Target Factor inhibitory activity of the peptide.

The term "purified peptide" refers to a compound which is substantially free of other compounds with which it may normally be associated in vivo. In the context of the invention, the term refers to homogenous Super-Sog, which homogenicity is determined by reference to purity standards known to those of ordinary skill in the art (e.g., purity sufficient to allow the N-terminal amino acid sequence of the protein to be obtained). Super-Sog may be obtained from embryonic insects, such as *Drosophilia*, or insect cell lines, and purified to homogenicity using means known to those skilled in the art, such as affinity chromatography.

Recombinant Super-Sog can also be produced in vitro or in vivo through expression of a polynucleotide sequence which encodes Super-Sog (e.g., SEQ ID NO:1). In general, prokaryotes are used for cloning of DNA sequences in constructing recombinant expression vectors. For example, *E. coli* K12 strain 294 (ATCC Accession No. 31446) may be particularly useful. Prokaryotes also are used for expression. The aforementioned strain, as well as *E. coli* W3110 (ATTC Accession No. 27325), bacilli such as *Bacillus subtilus*, and other enterobacteriaceac such as *Salmonella typhimurium* or *Serratia marcescans*, and various *pseudomonas* species may also be used for expression.

Non-viral plasmid vectors which may be used in the invention contain promoters and control sequences which are derived from species compatible with the host cell. The vector ordinarily carries a replication site as well as marker sequences which are capable of providing phenotypic selection in transformed cells. For example, *E. coli* is typically transformed using pBR322, a plasmid derived from an *E. coli* species (Bolivar, et al., *Gene*, 2:95, 1977). pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA construction.

Expression may also be achieved using RNA or DNA viruses, including retroviruses, adenoviruses, herpes virus, vaccinia and adeno-associated viruses. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), human immunodeficiency virus (HIV-1) and Rous Sarcoma Virus (RSV). Adeno-associated viruses are especially useful for their stable expression and relative lack of adverse side effects when delivered in vivo.

A number of viral vectors can incorporate multiple genes. All of these vectors can transfer or incorporate a gene for a selectable marker so that transduced cells can be identified and generated. By inserting one or more sequences of interest into the viral vector, along with another gene which encodes the ligand for a receptor on a specific target cell, for example, the vector is now target specific.

Further, in addition to prokaryotes, eukaryotic microbes such as yeast cultures may also be used. *Saccharomyces cerevisiae*, or common baker's yeast is the most commonly used eukaryotic microorganism for use in in vitro expression of polynucleotides, although a number of other strains are commonly available.

Suitable promoting sequences for use with yeast hosts include the promoters for 3-phosphoglycerate kinase (Hitzeman, et al., *J. Biol. Chem.*, 255:2073, 1980) or other glycolytic enzymes (Hess, et al. *J. Adv. Enzyme Reg.* 7:149, 1968; and Holland, *Biochemistry*, 17:4900, 1973) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degraded enzymes associated with nitrogen metabolism, metallothionine, glyceraldehyde-3-phosphate dehydrogenase, and enzymes responsible for maltose and galactose utilization. Yeast enhancers also are advantageously used with yeast promoters.

Super-Sog can also be readily synthesized by conventional techniques, such as the solid phase synthesis techniques as described in Gutierrez, et al., FEBS Letters, 372:39-43 (1995), the disclosure of which is incorporated herein by this reference to illustrate knowledge in the art concerning techniques for the production of synthetic peptides.

Briefly, commonly used methods such as t-Boc or Fmoc protection of alpha-amino groups are suitable for use in synthesizing Super-Sog of the invention. Both methods involve stepwise syntheses whereby a single amino acid is added at each step starting from the C terminus of the peptide (see, Coligan, et al., Current Protocols in Immunology, Wiley Interscience, 1991, Unit 9). Peptides of the invention can also be synthesized by various well known solid phase peptide synthesis methods, such as those described by Merrifield (J. Am. Chem. Soc., 85:2149, 1962), and Stewart and Young (Solid Phase Peptides Synthesis, Freeman, San Francisco, 1969, pp 27-62), using a copoly (styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with 1% acetic acid solution which is then lyophilized to yield the crude material. This can normally be purified by such techniques as gel filtration on a "SEPHADEX G-15" or "SEPHAROSE" affinity column. Lyophilization of appropriate fractions of the column will yield the homogeneous peptide or peptide derivatives, which can then be characterized by such standard techniques as amino acid analysis, thin layer chromatography, high performance liquid chromatography (HPLC), ultraviolet absorption spectroscopy, molar rotation, solubility, and quantitated by the solid phase Edman degradation.

The synthesis objective is to produce peptides whose charge distribution is similar to that in the native sequence. The selection of resins and post-synthesis treatments for each peptide will therefore be optimized for this result. In particular, resins that yield a free carboxy group are useful to generate peptides representing the C-terminal of a protein. Subsequently, the N-terminal will be acetylated. Resins that yield an aminated C-terminal are useful to generate internal peptides and peptides representing the N-terminal region. For generation of internal sequence peptides, the N-terminal is acetylated, whereas for generation of N-terminus peptides, the N-terminal is free.

In order to increase the bioavailability of Super-Sog, the peptide may be synthesized using standard Fmoc or t-Boc chemistries with amino acid derivatives in D-conformation. Alternatively, sequences with reduced peptide bonds in positions susceptible to proteolysis may be synthesized according to, for example, Meyer et al., J. Med. Chem., 38:3462-3468 (1995) (incorporated herein for reference). Briefly, such peptides are synthesized using a Fmoc/tert-butyl strategy, and the Y(CH$_2$NH) bonds, or reduced bonds, are introduced via reductive alkylation of the N-terminal amino group of the growing peptide with a Fmoc-Na-protected amino aldehyde.

To increase the efficacy of selected peptides so they can exert their physiological effect for longer periods of time, the following refinements to Super-Sog may be made using techniques which those of ordinary skill in the art will be familiar with or can readily ascertain.

The acetylation of an N-terminal amino group or the choice of N-terminal amino acid can dramatically improve the α-helical stability (Chakrabartty, et al., Proc. Natl. Acad. Sci. USA 90:11332-11336 (1993); Jarvis, et al., J. Biol. Chem. 270: 1323-1331 (1995)) and biological activity of a peptide (Dooley, et al., Science 266:2019-2022 (1994)). N-terminal acetylation has also been described as a factor which contributes to the stabilization of coil forming peptides (Greenfield, et al., Protein Science 3:402-410 (1994)) and to increase resistance to proteolytic degradation by exopeptidases (Abiko, et al., Chem. Pharm. Bull. 39:752-756 (1991)). Super-Sog may therefore be modified to have enhanced activity and stability by acetylation of their N-terminal.

D-isomers of Super-Sog are also desirable for their resistance to proteolytic degradation in vivo. It is well recognized that L-bond peptides are susceptible to proteolytic degradation, restricting their application as drugs. However, this obstacle has been successfully bypassed in some cases by synthesizing analogues which contain D-bond amino acids or non-natural amino acids. The addition of a single D-amino acid at the C-terminal position is enough to enhance the resistance to proteolytic degradation by exopeptidases, without significantly altering the secondary structure of the peptide (Abiko, supra). Resistance to endopeptidases can be achieved by including individual non-cleavable non-peptidic bonds in points in the peptide sequence that are specially sensitive to enzymatic degradation (Meyer, et al., J. Med. Chem. 38:3462-3468 (1995); Guichard, et al., Peptide Research 7:308-321 (1994)). Reverse amide bonds Y[NHCO], reduced amide bonds Y[CH$_2$NH] or retro-reduced bonds Y[NHCH$_2$] can be used as surrogates of the amide link [CONH] in ESUPs of the invention. Reduced amide links are preferred, since they result only in minor destabilization of a-helices (Dauber-Osguthorpe, et al., Int. J. Pep. Prot. Res. 38:357-377 (1991)). In Sog, the cleavage site for the Tolloid protease near the COOH end of CR-1 is a convenient site for modification of Super-Sog to increase its resistance to proteolytic degradation.

Alternatively, Super-Sog can be synthesized in an all-D-conformation. All-D-peptides can be equally active as the original all-L-peptides (Merrifield, et al., Ciba Foundation Symposium 186:5-20 (1994); Wade, et al., Proc. Natl. Acad. Sci. USA 87:4761-4765 (1990)), capable of successfully resisting enzymatic degradation and less immunogenic than their all-L-analogues (King, et al., J. Immunol. 153:1124-1131 (1994)).

III

Pharmaceutical Compositions of Super-Sog and Super-Sog Kits

Pharmaceutically useful compositions of Super-Sog are prepared by mixing the peptide with physiologically acceptable carriers. Such carriers will be nontoxic to recipients at the dosages and concentrations employed. Ordinarily, the preparation of such compositions entails combining the particular protein with buffers, antioxidants such as ascorbic acid, low molecular weight (less than about 10 residues) polypeptides, proteins, amino acids, carbohydrates including glucose or dextrins, chelating agents such as EDTA, glutathione and other stabilizers and excipients.

Such compositions may be lyophilized for storage and will be reconstituted according to pharmaceutically acceptable means; i.e., suitably prepared and approved for use in the desired application. A sodium chloride free buffer is preferred for use as a reconstituting agent. Whatever its form, the composition product will be placed into sterile containers (e.g., ampules) for storage and transportation.

For targeted delivery of Super-Sog, a colloidal dispersion system is useful. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2-4.0 µm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes encoding the antisense polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingo-lipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidyicholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Super-Sog kits are also provided by the invention. In diagnostic and research applications such kits may include any or all of the following: assay reagents, buffers and Super-Sog protein and/or homologues, Super-Sog coding recombinant expression vectors, oligonucleotide and other hybridization probes and/or primers, and/or a suitable assay device. A therapeutic product may include sterile saline or another pharmaceutically acceptable emulsion and suspension base for use in reconstituting lyophilized Super-Sog or Super-Sog antibody suspensions, suitably labeled and approved containers of Super-Sog or Super-Sog antibody compositions, and kits containing these products for use in connection with the diagnostic kit components as described above.

Such a kit may also comprise a carrier means being compartmentalized to receive in close confinement one or more container means such as vials, tubes, and the like, each of the container means comprising one of the separate elements to be used in the method.

For example, one of the container means may comprise a hybridization probe that is or can be detectably labelled. A second container may comprise a cell lysis buffer. The kit may also have containers holding nucleotide(s) for amplification of the target nucleic acid sequence and/or a container comprising a reporter-means, such as a biotin-binding protein, such as avidin or streptavidin, bound to a reporter molecule, such as an enzymatic, fluorescent, or radionuclide label.

IV

Methods and Dosages for In Vivo Delivery of Super-Sog

A "therapeutically effective dosage" of Super-Sog composition in a pharmaceutically acceptable carrier will be that dosage which produces a therapeutic benefit in a host that can also be provided by another BMP-4 inhibitor (e.g., Sog), but is provided in lieu of such other inhibitor. In particular, because Super-Sog's affinity for Dpp is in the picomolar range, it is predictable to those of ordinary skill in the art that dosing regimes (including dosing concentrations and schedules) applied to other pharmaceutical compounds which target receptor-ligand interactions with affinities in the picomolar range will be useful for SuperSog (depending on the patient's condition and the medical judgment of the clinician).

Analogous examples include neurotransmitter antagonists, serotonin uptake inhibitors and GABA antagonists (see, e.g., Boritzki, et al., *Invest. New Drugs*, 14:295-303 (1996) and Coy, et al., *J. Biol. Chem.*, 25:14691-14697 (1989)). Based on these analogies, and evidence obtained through administration of SuperSog to flies and frogs, suitable concentrations of SuperSog for use in therapeutic applications range from about 0.01 to 200 nanomolar, with suitable concentrations for many applications falling within the range of about 0.1 to 50 nanomolar.

Depending on the desired clinical result, the dosage will be administered by means best suited to reach target tissue; e.g., for the scalp, a topical route of administration may be preferred while for neurogenesis, grafting of cells transformed with a recombinant expression vector encoding Super-Sog may be a better choice (see, e.g., commonly assigned U.S. Pat. Nos. 5,082,670; 5,529,774 and 5,650,148, incorporated herein for reference regarding skill in the art concerning ex vivo gene therapy and cell grafting to nervous tissue in vertebrates).

Super-Sog can also be labeled with a paramagnetic isotope for purposes of in vivo imaging, as in magnetic resonance imaging (MRI) or electron spin resonance (ESR) techniques. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

Depending on the desired clinical target, Super-Sog may be delivered to a host using any available method and route suitable for drug delivery, including ec vivo methods (e.g., delivery of cells incubated or transfected with a Super-Sog encoding polynucleotide) as well as systemic or localized routes. However, those of ordinary skill in the art will appreciate that parenteral methods of administration, especially by non-systemic routes, will generally be preferred for avoidance of peptide degradation in vivo.

Intranasal administration means include inhalation of aerosol suspensions or insufflation of the polynucleotide compositions of the invention. Nebulizer devices suitable for delivery of polynucleotide compositions to the nasal mucosa, trachea and bronchioli are well-known in the art and will therefore not be described in detail here. For general review in regard to intranasal drug delivery, those of ordinary skill in the art may wish to consult Chien, *Novel Drug Delivery Systems*, Ch. 5 (Marcel Dekker, 1992).

Examples of means for delivering drugs to the skin are topical application of a suitable pharmaceutical preparation, transdermal transmission, injection and epidermal administration.

For transdermal transmission, absorption promoters or iontophoresis are suitable methods. For review regarding such methods, those of ordinary skill in the art may wish to consult Chien, supra at Ch. 7. Iontophoretic transmission may be accomplished using commercially available "patches" which deliver their product continuously via electric pulses through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product is the LECTRO PATCH trademarked product of General Medical Company of Los Angeles, Calif. This product electronically maintains reservoir electrodes at neutral pH and can be adapted to provide dosages of differing concentrations, to dose continuously and/or to dose periodically. Preparation and use of the patch should be performed according to the manufacturer's printed instructions which accompany the LECTRO PATCH product; those instructions are incorporated herein by this reference.

Intraparenchymal administration to the brain, as well as administration to the central nervous system, may be performed by known means including grafting drug expressing transformed host cells onto the target tisue and injection of the drug by microsyringe directly into tissue. Those of skill in the art may wish to consult *Neural Grafting in the Mammalian CNS*, Bjorklund and Steveni, eds., (1985) as well as U.S. Pat. Nos. 5,082,670 and 5,529,774, each of which is incorporated herein to illustrate the level of skill in the art of drug delivery to the brain and CNS.

Systemic administration involves invasive or systemically absorbed topical administration of pharmaceutical preparations. Topical applications as well as intravenous and intramuscular injections are examples of common means for systemic administration of drugs.

V

Diagnostic Uses for Super-Sog

Hyperactive BMP-4 signalling is indicative of diminished Super-Sog-like antagonism of BMP-4. Measurement of Super-Sog-like activity in vivo therefore would be of diagnostic value with respect to conditions causatively associated with hyperactive BMP-4 signalling. For in vitro measurements, anti-Super-Sog antibodies may be used diagnostically (e.g., to detect Super-Sog in a biological cell sample or monitor the level of its expression). A suitable cell sample may be derived from tissue biopsies, sputum specimens, blood specimens or urinary specimens. Germline cells may be obtained from any convenient source, such as skin, blood, or hair follicles.

Super-Sog and its structural homologue in vertebrate species may be detected and/or bound using Super-Sog antibodies in either liquid or solid phase immunoassay formats (when bound to a carrier). Examples of well-known carriers for use in solid-phase assay formats include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation. Examples of types of immunoassays which can utilize monoclonal antibodies of the invention are competitive and non-competitive immunoassays in either a direct or indirect format.

Specific examples of such immunoassays are the radioimmunoassay (RIA) and the sandwich (immunometric) assay. Using the Super-Sog antibodies of the invention can be done utilizing immunoassays which are run in either the forward, reverses or simultaneous modes, including immunohistochemical assays on physiological samples. Super-Sog antibodies and peptides can be used to measure Target Factor inhibition and binding using Super-Sog antibodies (see, e.g., the binding assay protocols described in Grazioli, et al., *Int. J. Immunopharma.*, 14:637-642 (1992) and Hosang, *J. Cell. Biochem.*, 29:265-273 (1985)). Those of skill in the art will know, or can readily discern other immunoassay formats without undue experimentation.

Super-Sog and Super-Sog homologues may also be detected in cell samples through hybridization of labelled probes or primers which bind the gene which encodes Super-Sog. Hybridization probes and primers generally do not encode Super-Sog but nonetheless are capable of hybridizing with DNA encoding Super-Sog. Such probes and primers are usually oligonucleotides; i.e., either a single standed polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

Such oligonucleotides may be detectably labelled with a detectable substance such as a fluorescent group, a radioactive atom or a chemiluminescent group by known methods and used in conventional hybridization assays.

The Super-Sog antibodies of the invention may also be detectably labelled. There are many different labels and methods of labeling known to those of ordinary skill in the art.

Examples of the types of labels which can be used in the present invention include enzymes, radioisotopes, fluorescent compounds, colloidal metals, chemiluminescent compounds, and bio-luminescent compounds. Those of ordinary skill in the art will know of other suitable labels for binding to the anti-Super-Sog antibodies of the invention, or will be able to ascertain such, using routine experimentation. Furthermore, the binding of these labels to the Super-Sog antibodies of the invention can be done using standard techniques common to those of ordinary skill in the art. Another labeling technique which may result in greater sensitivity consists of coupling the antibodies to low molecular weight haptens. These haptens can then be specifically detected by means of a second reaction. For example, it is common to use haptens for this purpose such as biotin, which reacts with avidin.

Monitoring of the effect of Super-Sog applied therapeutically may be made by measuring BMP-4 levels at the onset, and through the duration, of therapy. Such tests may be performed on fluid or cell samples in vitro, or through in vivo imaging. In using the anti-Super-Sog antibodies of the invention for the in vivo detection of antigen having a peptide of the invention, the detectably labeled monoclonal antibody is given in a dose which is diagnostically effective. The term "diagnostically effective" means that the amount of detectably labeled Super-Sog antibody is administered in sufficient quantity to enable detection of the site having cells which express Super-Sog.

For this purpose, the concentration of detectably labeled Super-Sog antibody which is administered should be sufficient such that it is detectable compared to the background. Further, it is desirable that the detectably labeled Super-Sog antibody be rapidly cleared from the target tissue in order to give the best target-to-background signal ratio.

For in vivo imaging, the type of detection instrument available is a major factor in selecting a given detectable label; e.g., a radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized.

Ideally, a radioisotope used for in vivo imaging will lack a particle emission, but produce a large number of photons in the 140-250 keV range, which may be readily detected by conventional gamma cameras. Typical examples of metallic ions which can be bound to the ESUPs of the invention are $^{111}$In, $^{97}$Ru, $^{67}$Ga, $^{68}$Ga, $^{72}$As, $^{89}$Zr, $^{90}$Y, and $^{201}$Tl.

As a rule, the dosage of detectably labeled Super-Sog antibody for in vivo diagnosis will vary depending on such factors as age, sex, and extent of disease of the individual. The dosage of antibody can vary from about 0.01 mg/m$^2$, to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tissue, and other factors known to those of skill in the art.

Examples illustrating the construction and use of the invention are provided below. These examples do not limit the scope of the invention, which is defined by the appended claims. Standard abbreviations (e.g., "ml" for milliliters) are used in the examples unless otherwise noted.

EXAMPLE I

Effect of Super-Sog on Wing Structure in *Drosophilia*

As a convenient reference point for the effect of Super-Sog on Dpp activity in *Drosophilia* (modeling the capacity of Super-Sog to modulate BMP-4 activity in vertebrates, if not the outcome of that modulation), Dpp signalling consequences in wing morphogenesis are scored for the development of one or more of four phenotypes characteristic of Dpp suppression: (1) missing sections of wing veins; (2) thickened wing veins; (3) decreased distances separating wing veins; and (4) decreased wing length, each as compared to wing phenotypes in normal flies (see, e.g., Yu, et al., *Development*. 122: 4033-4044 (1996), especially FIG. 1 comparing Dpp-active and Dpp-suppressed wing phenotypes in adult flies).

Wild-type Sog antagonizes Dpp to block wing formation (phenotype 1). For comparison, a broader spectrum vertebrate BMP-4 antagonist (noggin) which shares a fairly high degree of coding sequence homology with Super-Sog blocks some wing formation (phenotype 1), shortens the distance between wing veins through fusion (phenotype 3) and produces shorter wings (phenotype 4) in *Drosophilia*.

Super-Sog elicits all four Dpp-suppression phenotypes. Its effect on the development of phenotypes 1, 3 and 4 is similar to the effects produced by noggin, although Super-Sog can stimulate fusion of all 5 *Drosophilia* wing veins while noggin influences fusion of only 2 sets of the veins (vein 2 with 3 and vein 4 with 5). Preliminary results indicate comparable results (in different phenotypic models) are produced as a consequence of Super-Sog suppression of BMP-4 in frogs.

The invention having been fully described, modifications thereto may be apparent to those of ordinary skill in the art. All such modifications are included within the scope of the claimed invention.

SUMMARY OF SEQUENCES

SEQ ID NO:1 is the nucleotide sequence which codes for a Super-Sog polypeptide.
SEQ ID NO:2 is the predicted amino acid sequence of Super-Sog based on SEQ ID NO:1.
SEQ ID NO:3 is a compilation of the nucleotide sequence SEQ ID NO:1) coding for a Super-Sog polypeptide and 33 amino acids of the pUAS expression vector coded by the nucleotide sequence following NotI.
SEQ ID NO:4 is the predicted amino acid sequence of Super-Sog and 33 amino acids of the pUAS expression vector encoded by SEQ ID NO:3
SEQ ID NO:5 is the nucleotide sequence coding for a Super-Sog peptide which includes a mutation (W-A) in the CR-1 sequence.
SEQ ID NO:6 is the predicted amino acid sequence of the Super-Sog peptide, which includes a mutation (W-A) in the CR1 sequence encoded by SEQ ID NO:5.
SEQ ID NO:7 is the nucleotide sequence coding for a Super-Sog peptide which is modified 5' of the NotI restriction site sequence of SEQ ID NO:3.
SEQ ID NO:9 is a partial amino acid sequence for noggin encompassing a region of homology to Super-Sog.
SEQ ID NO:10 is a partial amino acid sequence for noggin encompassing a region of homology to Super-Sog.
SEQ ID NO:11 is the full-length nucleotide sequence coding for wild-type Sog.
SEQ ID NO:12 is the predicted amino acid sequence of wild-type Sog based on SEQ ID NO:11.

What is claimed is:

1. A purified peptide consisting of the amino acid sequence of amino acids 1-292 of the *Drosophila* Sog protein.

2. A pharmaceutical composition comprising the peptide of claim 1.

* * * * *